United States Patent
Rezach et al.

(10) Patent No.: US 11,801,074 B1
(45) Date of Patent: Oct. 31, 2023

(54) SPINAL IMPLANT SYSTEM AND METHOD

(71) Applicant: Warsaw Orthopedic, Inc., Warsaw, IN (US)

(72) Inventors: William Alan Rezach, Covington, TN (US); Ahmad Alsaffar, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/744,974

(22) Filed: May 16, 2022

(51) Int. Cl.
*A61B 17/70* (2006.01)
*A61B 17/86* (2006.01)
*A61B 17/00* (2006.01)

(52) U.S. Cl.
CPC ...... *A61B 17/7049* (2013.01); *A61B 17/7032* (2013.01); *A61B 17/8685* (2013.01); *A61B 17/8695* (2013.01); *A61B 2017/00477* (2013.01)

(58) Field of Classification Search
CPC ........... A61B 17/7049; A61B 17/7032; A61B 17/8685; A61B 17/8695; A61B 2017/00477
USPC ....... 606/250, 264, 265, 266, 267, 268, 269, 606/270, 272, 278, 305, 308, 328
See application file for complete search history.

(56) References Cited

U.S. PATENT DOCUMENTS

| | | | |
|---|---|---|---|
| 8,430,917 B2 | 4/2013 | Rezach | |
| 9,615,867 B2 | 4/2017 | Picetti et al. | |
| 9,622,788 B2 | 4/2017 | Rezach et al. | |
| D842,479 S | 3/2019 | Rezach et al. | |
| 10,695,100 B2 | 6/2020 | May et al. | |
| 10,736,665 B2 | 8/2020 | Bobbitt et al. | |
| 2003/0199873 A1* | 10/2003 | Richelsoph | A61B 17/7037 606/264 |
| 2005/0182410 A1* | 8/2005 | Jackson | F16B 35/047 606/300 |
| 2006/0083603 A1* | 4/2006 | Jackson | F16B 33/02 411/386 |
| 2010/0036433 A1* | 2/2010 | Jackson | A61B 17/7037 606/305 |
| 2016/0166289 A1* | 6/2016 | Alsup | A61B 17/70 606/253 |
| 2017/0042584 A1* | 2/2017 | Lehmann, Jr. | A61B 17/7038 |
| 2017/0086895 A1* | 3/2017 | Barra | A61B 17/8605 |
| 2019/0183535 A1* | 6/2019 | May | A61B 17/7032 |

FOREIGN PATENT DOCUMENTS

| | | | | |
|---|---|---|---|---|
| EP | 3566665 A1 | * | 11/2019 | ......... A61B 17/7001 |
| WO | WO-2005018471 A1 | * | 3/2005 | ......... A61B 17/7037 |

* cited by examiner

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A bone fastener includes a head including a first receiver defining an implant cavity and a distal portion defining a plurality of adjacent grooves. The head further includes a second receiver defining an implant cavity. A first resilient member is configured for disposal within the plurality of adjacent grooves and a second resilient member is configured for disposal within the plurality of adjacent grooves. A shaft is aligned with the first receiver and is configured to engage tissue. Systems, surgical instruments, spinal constructs, implants and methods are disclosed.

20 Claims, 8 Drawing Sheets

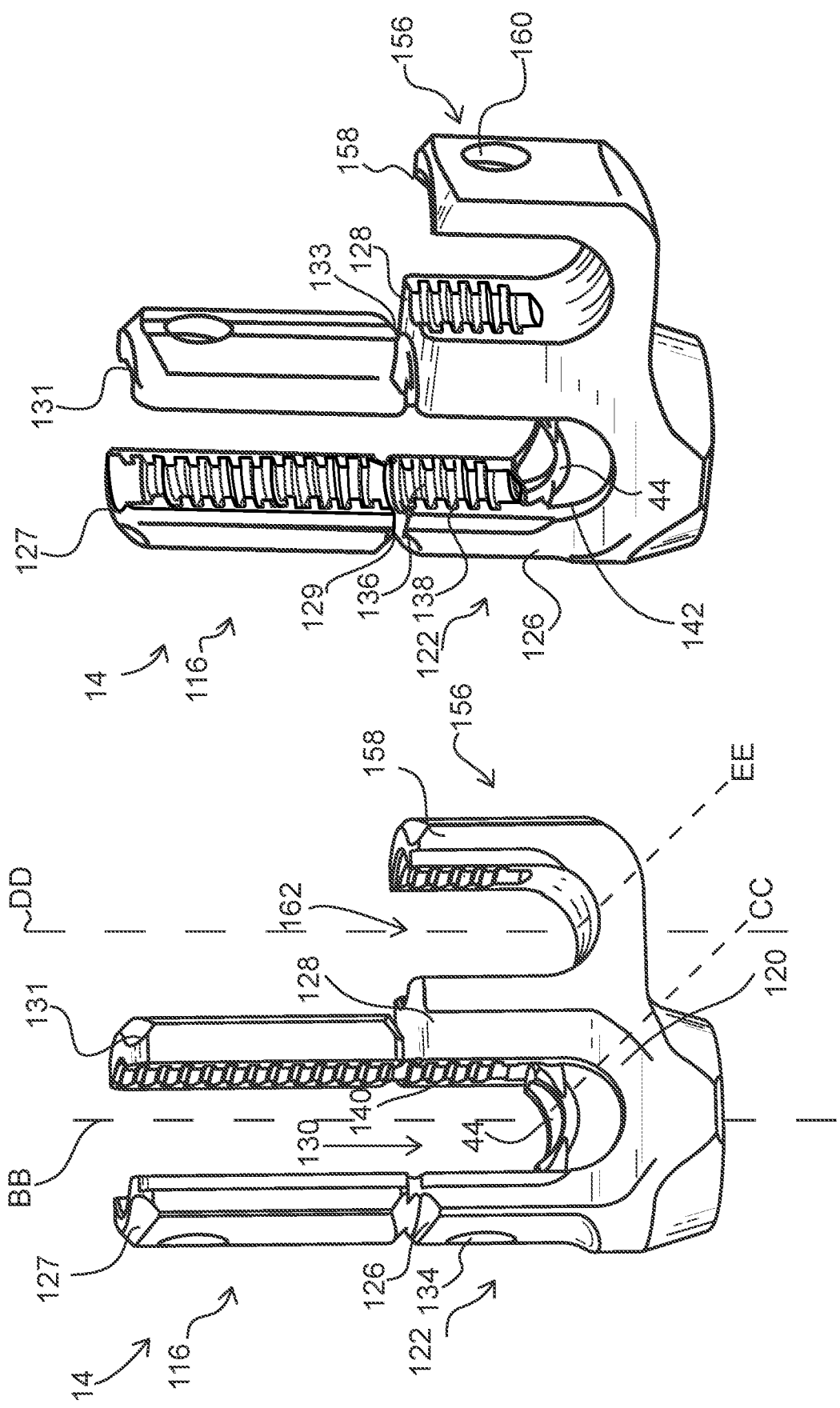

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener includes a head including a first receiver defining an implant cavity and a distal portion defining a plurality of adjacent grooves. The head further includes a second receiver defining an implant cavity. A first resilient member is configured for disposal within the plurality of adjacent grooves and a second resilient member is configured for disposal within the plurality of adjacent grooves. A shaft is aligned with the first receiver and is configured to engage tissue. In some embodiments, systems, surgical instruments, spinal constructs, implants and methods are disclosed.

In one embodiment, the bone fastener includes a head including arms that define a first rod slot and a second rod slot, the rod slots being separate and adjacent. The head further includes a distal portion defining a plurality of adjacent grooves. A shaft is attached with the head for multi-axial movement. The shaft is aligned with the first rod slot and is configured to engage tissue. A first ring is configured for disposal within the plurality of adjacent grooves and a second ring is configured for disposal within the plurality of adjacent grooves. A crown is disposed with the first rod slot.

In one embodiment, a spinal implant system is provided. The spinal implant system includes a bone fastener having a head including a first rod slot and a distal portion defining a plurality of adjacent grooves. The head further includes a second rod slot. A first resilient member and a second resilient member are disposable within the plurality of adjacent grooves. A shaft is aligned with the first rod slot and is configured to engage tissue. The spinal implant system further includes a first spinal rod and a second spinal rod.

BRIEF DESCRIPTION OF THE DRAWINGS

The present disclosure will become more readily apparent from the specific description accompanied by the following drawings, in which:

FIG. 7 is a perspective view of components of one embodiment of a system in accordance with the principles of the present disclosure;

FIG. 8 is a perspective view of the components of the system shown in FIG. 7.

DETAILED DESCRIPTION

Figure 1:
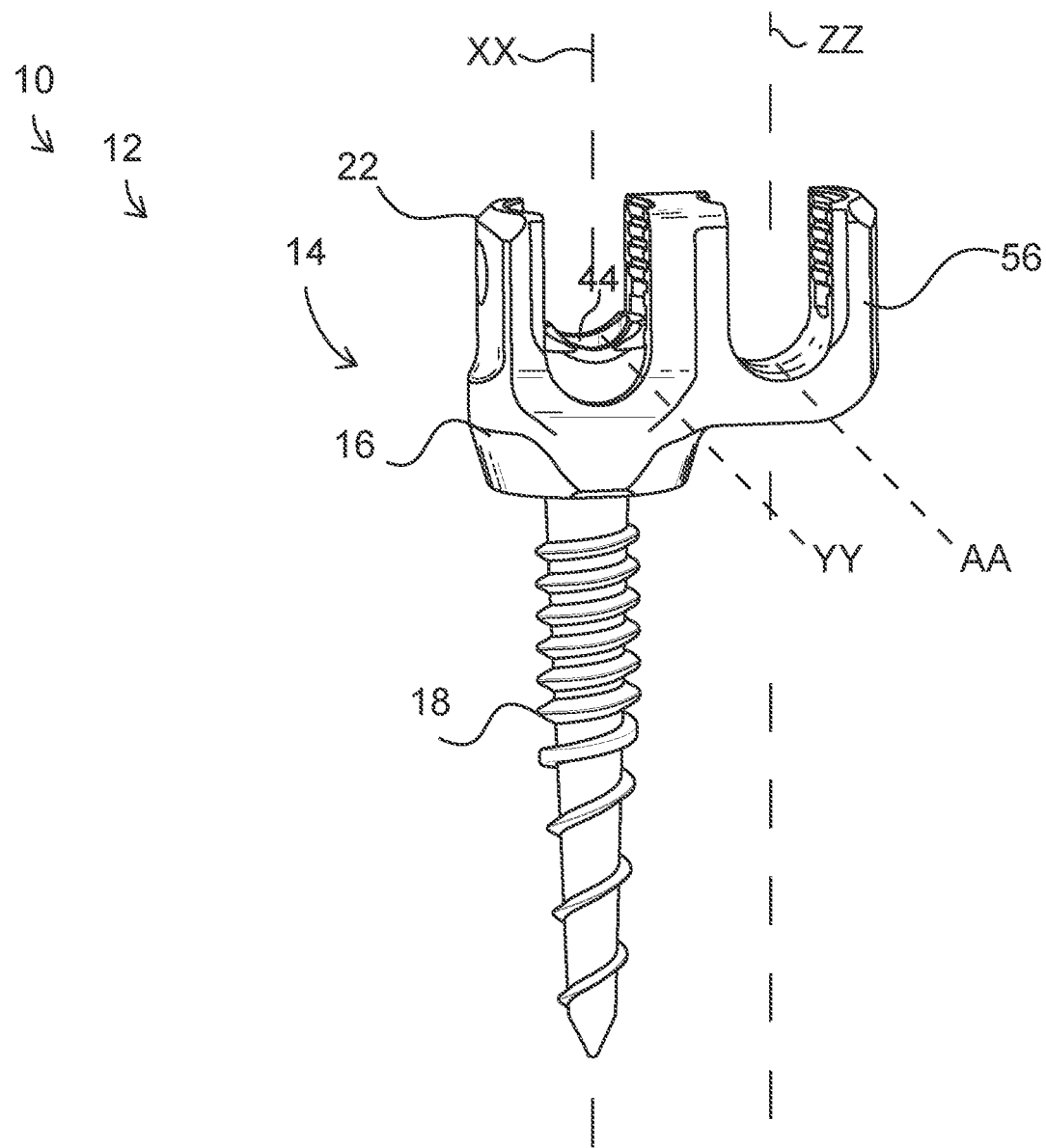
FIG. 1 is a side view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a bone fastener having a head including a first implant cavity and a second implant cavity, and a shaft configured for a modular connection with the head. In some embodiments, the bone fastener has a modular configuration including interchangeable heads and/or shafts. In some embodiments, the bone fastener includes a dual rod multi axial screw with a primary rod slot and a secondary rod slot. In some embodiments, the present surgical system includes a spinal construct having a modular bone fastener with a first implant receiver and a second implant receiver. In some embodiments, the modular bone fastener includes a shaft selected from one or more interchangeable shafts for interchangeable connection with a selected head described herein to comprise a bone fastener having a selected movement as described herein.

In some embodiments, the present surgical system includes a spinal construct including a screw shaft, a head, two resilient members, a crown and two spinal rods. In some embodiments, the spinal construct includes a bone fastener, including a modular dual rod multi axial screw. In some embodiments, the screw includes a dual rod head to facilitate rod-to-rod connection in a multiple-rod spinal construct. In some embodiments, the screw is modular and includes a pop-on assembly. In some embodiments, the modular screw increases visualization and access to a working space for a user.

In some embodiments, the present surgical system includes a modular dual rod multi axial screw including a head and a shaft. In some embodiments, the screw is configured for intraoperative assembly. In some embodiments, the screw is configured to accommodate in-situ and back table operating room screw assembly. In some embodiments, the screw is employed to treat adult deformity, cure failed fusion, and replace high stiffness spinal constructs.

In some embodiments, present surgical system includes a modular surgical system. In some embodiments, the system includes bone fastener, including a modular reduction dual rod multi-axial screw. In some embodiments, the reduction dual rod multi-axial screw includes a head and a shaft. In some embodiments, the head includes reduction tabs. In some embodiments, the reduction tabs enable rod reduction on a primary axis of the screw. In some embodiments, the rod is fixed to the head of the screw and the reduction tabs disengage after rod reduction. In some embodiments, the reduction dual rod multi-axial screw includes a smaller size footprint than a standard screw to facilitate improved positioning or manipulating of the orientation of an implant, for example, a spinal rod. In some embodiments, the modular surgical system facilitates an increase in screw distribution and decreases purchase cost.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, posterolateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct 12 that includes a bone fastener 14, as shown in FIG. 1. Bone fastener 14 includes a head 16 and a shaft 18. In some embodiments, head 16 is selected from a plurality of alternate heads and is configured for disposal with shaft 18 such that shaft 18 is interchangeable with the plurality of alternate heads, as described herein. In some embodiments, head 16 is selected for movement along a plurality of axes relative to shaft 18 in a multi-axial configuration to accommodate connection with one or more spinal rods, as described herein. In some embodiments, head 16 is selected for movement relative to shaft 18 through an angular range and disposable at a selected angle relative to shaft 18. In some embodiments, head 16 is selected for movement relative to shaft 18 through an angular range of 0-180 degrees. In some embodiments, the selected movement of head 16 includes rotation and/or pivotal movement of head 16 relative to shaft 18 about one or a plurality of axes. In some embodiments, the selected movement of head 16 includes rotation and/or pivotal movement of head 16 relative to shaft 18 through one or a plurality of planes. In some embodiments, the selected movement includes movement through one or more of transverse, vertical, horizontal, diagonal, coronal and/or sagittal planes of a body. In some embodiments, head 16 is selected for movement relative to shaft 18 in a fixed axis configuration.

Figure 2:
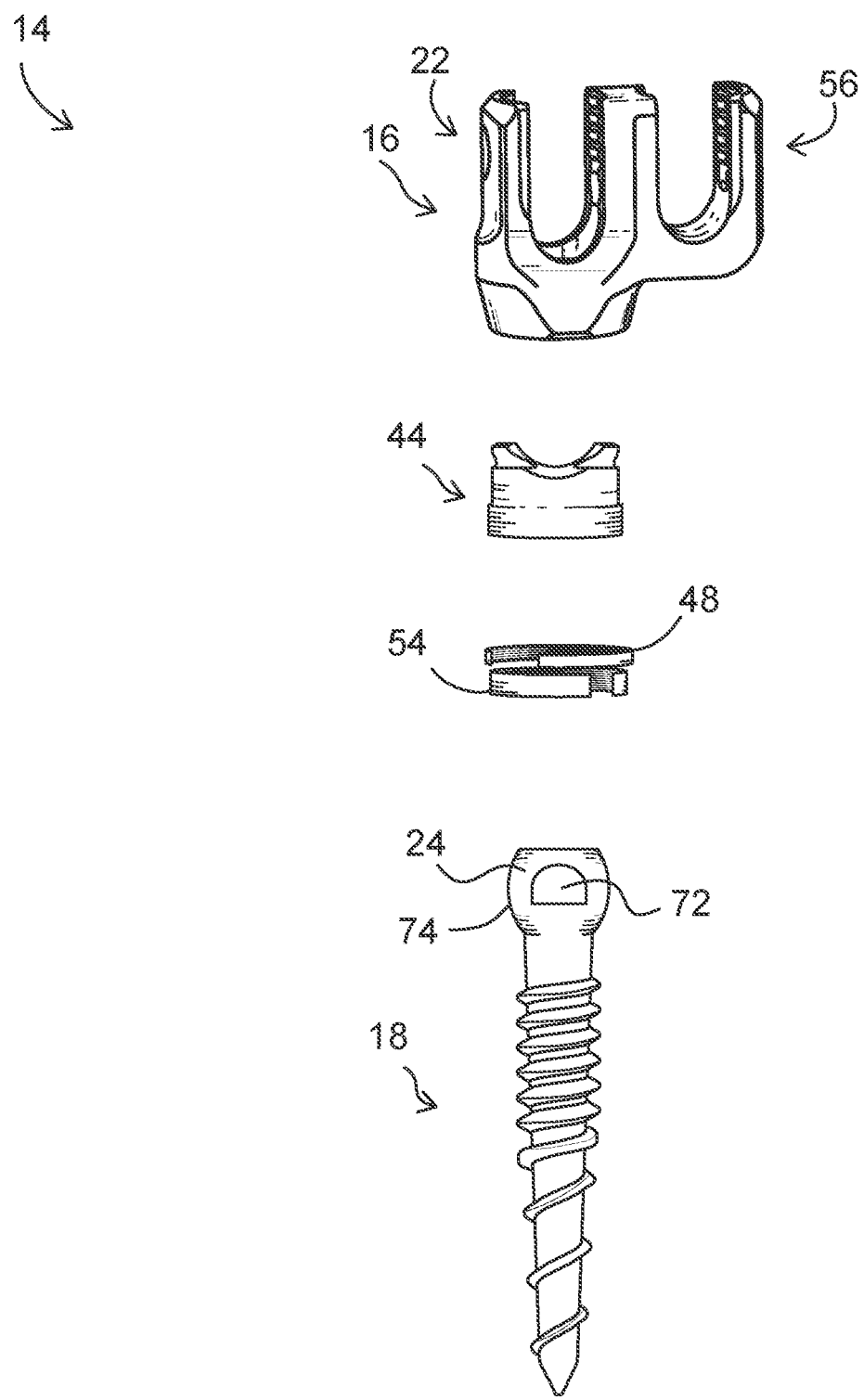
FIG. 2 is an exploded view of the components of the system shown in FIG. 1.
Figure 3:
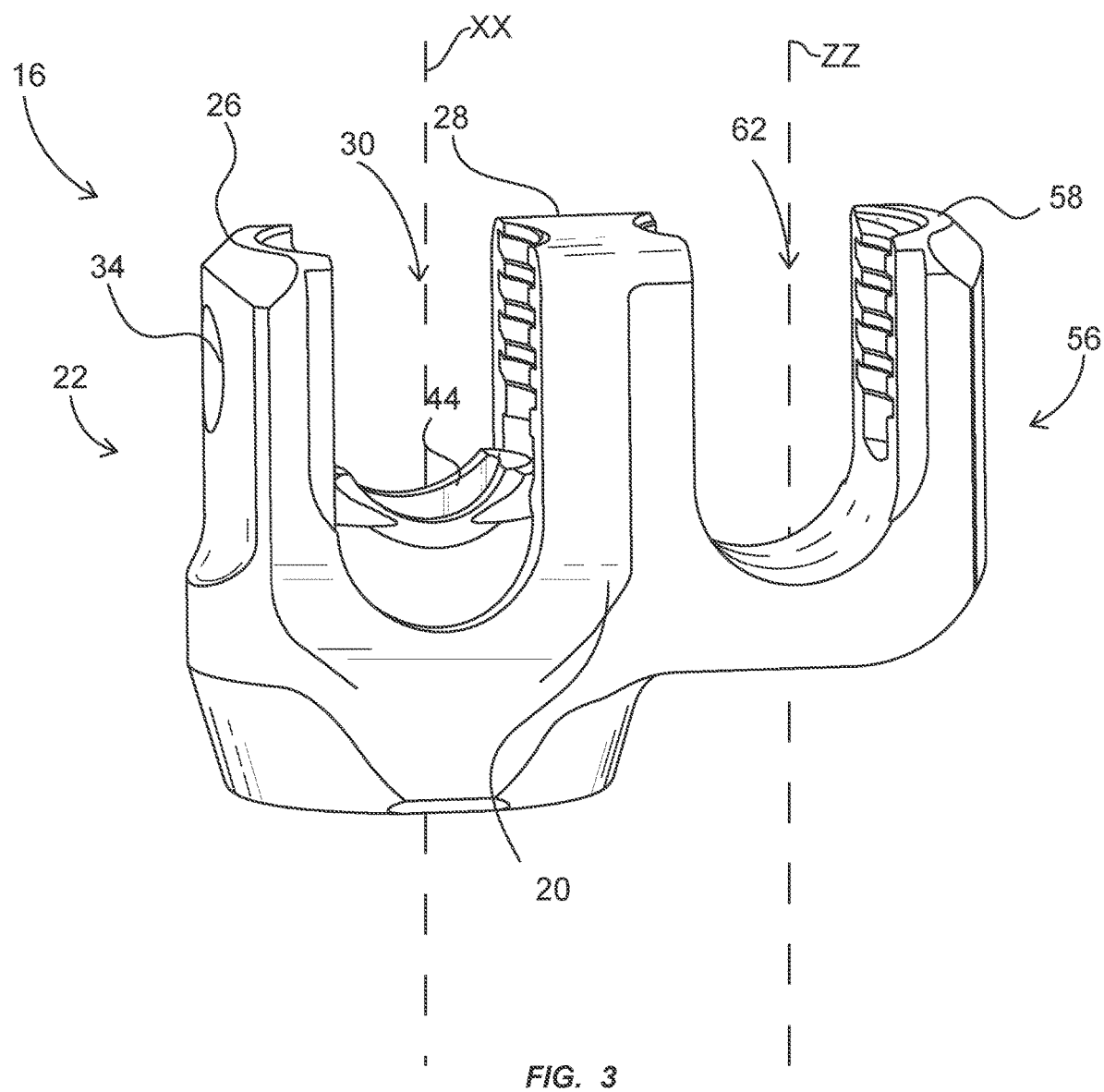
FIG. 3 is a perspective view of components of the system shown in FIG. 1.
Figure 4:
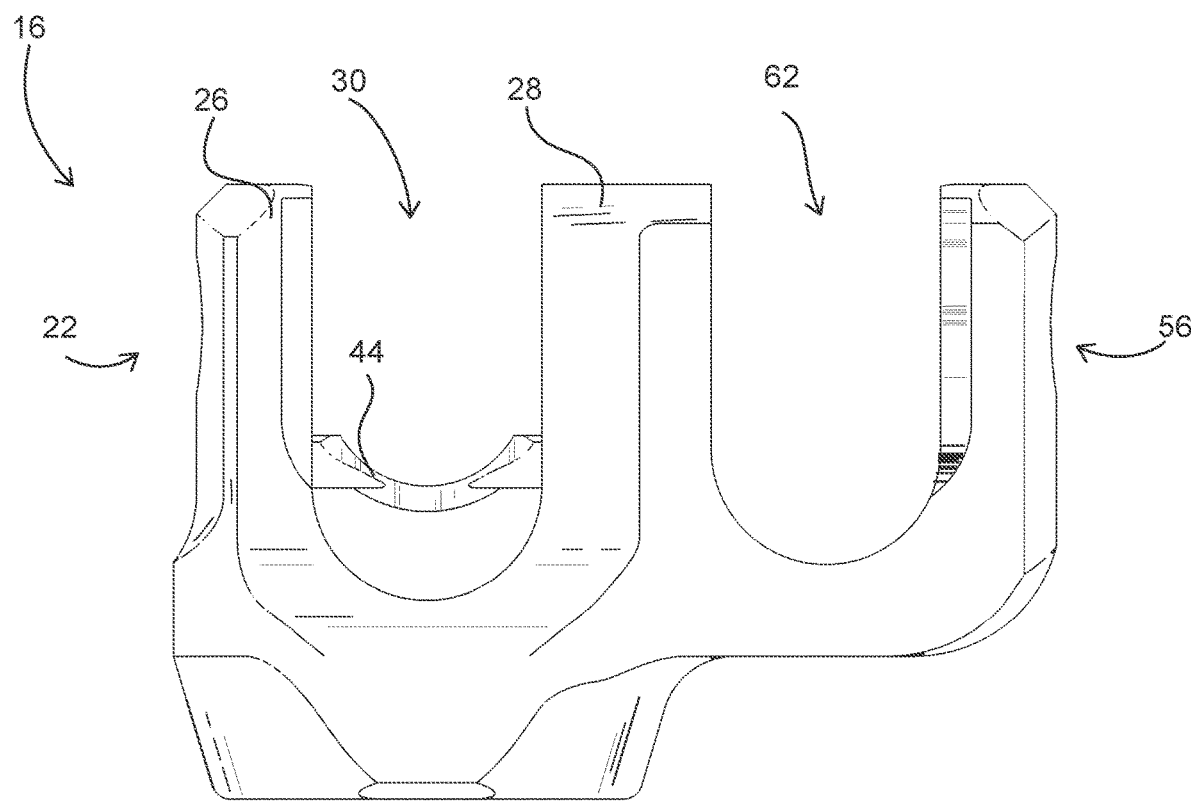
FIG. 4 is a side view of components of the system shown in FIG. 1.

Head 16 includes a body 20, as shown in FIG. 3. Body 20 includes a surface that defines a receiver 22. Receiver 22 is disposed in axial alignment with a head 24 of shaft 18, as shown in FIG. 2. Receiver 22 defines an axis XX and includes an arm 26 and an arm 28 spaced apart from arm 26. In some embodiments, shaft 18 is selectively movable relative to receiver 22 and/or axis XX through an angular range and disposable at a selected angle relative to receiver 22 and/or axis XX, similar to that described herein. In some embodiments, head 16 includes a w-shaped cross section configuration. In some embodiments, all or only a portion of head 16 may have alternate cross section configurations, for example, closed, V-shaped, w-shaped, W-shaped, oval, oblong triangular, square, polygonal, irregular, uniform, non-uniform, offset, staggered, and/or tapered.

Arms 26, 28 define an implant cavity, for example, a rod slot 30 therebetween. Rod slot 30 is configured for top loading of a spinal implant, for example, a spinal rod 32, as shown in FIG. 6. In some embodiments, rod slot 30 is configured for side loading or has a closed configuration. Arms 26, 28 each extend parallel to axis XX, as shown in FIG. 1. Arms 26, 28 each include an arcuate outer surface extending between a pair of side surfaces. In some embodiments, at least one of the outer surfaces and/or the side surfaces of arms 26, 28 have at least one recess or cavity 34 therein configured to receive an insertion tool, compression instrument and/or surgical instruments for manipulating bone fastener 14, as shown in FIG. 5.

Rod slot 30 is substantially U-shaped. Rod slot 30 defines and extends along an axis YY oriented transverse to axis XX, as shown in FIG. 1. In some embodiments, all or only a portion of rod slot 30 may have alternate cross section configurations, for example, closed, V-shaped, w-shaped, W-shaped, oval, oblong triangular, square, polygonal, irregular, uniform, non-uniform, offset, staggered, and/or tapered. Receiver 22 includes an inner surface 36, as shown in FIG. 5. A portion of surface 36 includes a thread form 38 located adjacent arm 26 and a thread form 40 located adjacent arm 28. Thread forms 38, 40 are each configured for engagement with a coupling member, for example, a set screw (not shown), to retain a spinal rod within rod slot 30. In some embodiments, surface 36 may be disposed with a set screw in alternate fixation configurations, for example, friction fit, pressure fit, locking protrusion/recess, locking keyway and/or adhesive. In some embodiments, all or only a portion of surface 36 may have alternate surface configurations to enhance engagement with a spinal rod and/or a set screw, for example, rough, arcuate, undulating, mesh, porous, semi-porous, dimpled and/or textured.

Figure 5:
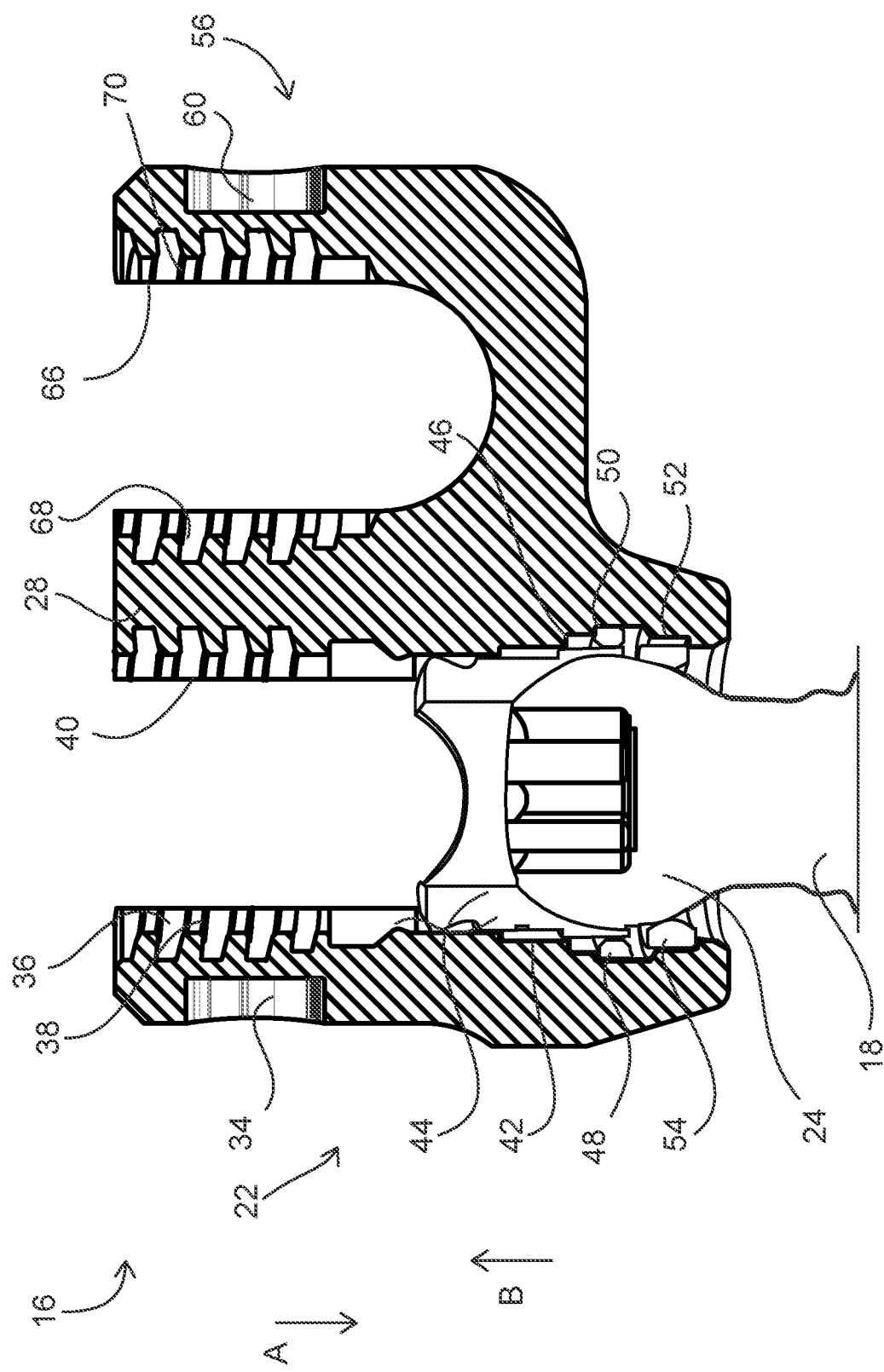
FIG. 5 is a cross section view of the components of the system shown in FIG. 4.
Figure 6:
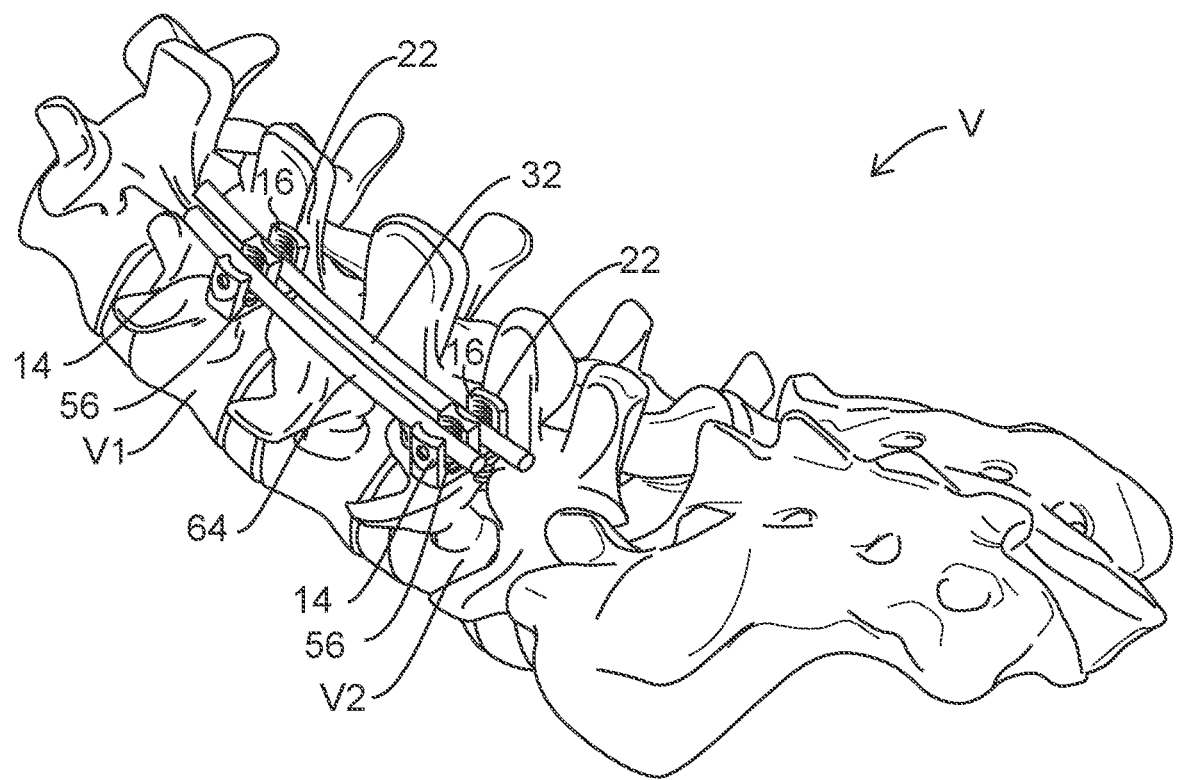
FIG. 6 is a perspective view of components of one embodiment of a system in accordance with the principles of the present disclosure disposed with vertebrae.

Receiver 22 includes a distal portion 42 configured for disposal of a crown 44, as shown in FIG. 5. Crown 44 is configured to facilitate engagement of spinal rod 32 with receiver 22. In some embodiments, crown 44 includes a concave or semi-spherical configuration to accommodate the outer surface of a portion of shaft 18 such that head 24 is rotatable relative to shaft 18 in a multi-axial configuration, as described herein. In some embodiments, a set screw is configured for engagement with spinal rod 32 to facilitate fixation and/or locking of spinal rod 32 with receiver 22. The set screw is disposable with receiver 22 between a non-locking orientation, such that spinal rod 32 is translatable relative to bone fastener 14 and a locked orientation, including provisional and permanent fixation, such that the set screw fixes spinal rod 32 with bone fastener 14.

An inner surface of portion 42 defines a circumferential upper groove 46, as shown in FIG. 5, for disposal of a resilient member, for example, a ring 48. Ring 48 is contractable in upper groove 46. Ring 48 includes a circumference that defines an opening, for example, a gap. In some embodiments, the gap is sized such that the gap has a length that is less than the height or the thickness of ring 48. In some embodiments, the gap is sized to allow ring 48 to translate through portion 42 by contracting circumferentially. The inner surface of portion 42 defines an expansion groove 50, as shown in FIG. 5.

The inner surface of portion 42 defines a circumferential lower groove 52 for disposal of a resilient member, for example, a ring 54, as shown in FIG. 5. Ring 54 is expandable in expansion groove 50. Ring 54 includes a circumference that defines an opening, for example, a gap. In some embodiments, the gap is sized such that the gap has a length that is less than the height or the thickness of ring 54. In some embodiments, the gap is sized to allow ring 54 to translate through portion 42 by contracting circumferentially. In some embodiments, rings 48, 54 facilitate manual engagement/connection of head 16 and shaft 18 such that shaft 18 is attached with head 16 in a non-instrumented snap-fit assembly, as described herein. In some embodiments, all or a portion of the inner surface is smooth, rough, arcuate, undulating, mesh, porous, semi-porous, dimpled and/or textured.

Head 16 includes a receiver 56, as shown in FIG. 3, similar to receiver 22, described herein. Receiver 56 defines an axis ZZ, as shown in FIG. 1 and includes arm 28 and an arm 58, as shown in FIG. 3. Arm 58 includes an arcuate outer surface extending between a pair of side surfaces. In some embodiments, at least one of the outer surfaces and/or the side surfaces of arm 58 have at least one recess or cavity 60 therein configured to receive an insertion tool, compression instrument and/or surgical instruments for manipulating bone fastener 14, as shown in FIG. 5. In some embodiments, shaft 18 is selectively movable relative to receiver 56 and/or axis ZZ through an angular range and disposable at a selected angle relative to receiver 56 and/or axis ZZ, similar to that described herein.

Arms 28, 58 are spaced apart to define an implant cavity, for example, a rod slot 62 therebetween. Receiver 22 is connected to receiver 56 via head 16 and arm 28 in a side by side and/or relatively parallel and adjacent orientation. As such, rod slots 30, 62 are disposed in a side by side and/or relatively parallel and adjacent orientation, and axis YY, and an axis AA are disposed in a relatively parallel orientation, for corresponding disposal of spinal rods therein, as shown in FIG. 1.

Rod slot 62 is configured for top loading of a spinal rod 64, as shown in FIG. 6. Arms 28, 58 each extend parallel to axis ZZ. In some embodiments, receivers 22, 56 form a w-shaped cross section configuration of head 16. In some embodiments, receiver 56 is disposed separate and spaced apart from receiver 22. In some embodiments, receiver 56 may be disposed in various orientations, for example, at angular orientations, such as acute or obtuse relative to receiver 22. In some embodiments, receiver 56 may be disposed offset or staggered relative to receiver 22, as described herein.

Rod slot 62 is disposed separate and apart from rod slot 30, and is substantially U-shaped. Rod slot 62 defines and extends along axis AA oriented parallel to axis YY. In some embodiments, all or only a portion of rod slot 62 may have alternate cross section configurations, for example, closed, V-shaped, w-shaped, W-shaped, oval, oblong triangular, square, polygonal, irregular, uniform, non-uniform, offset, staggered, and/or tapered. In some embodiments, rod slot 62 may be disposed in various orientations, for example, at angular orientations, such as acute or obtuse, relative to rod slot 30.

In some embodiments, receiver 56 is connected with receiver 22 in a relatively angled and adjacent orientation such that rod slots 30, 62 and axes YY, AA are disposed in a relatively angled orientation for corresponding disposal of spinal rods therein. In some embodiments, receiver 56 is connected to receiver 22 in a relatively angled and adjacent orientation such that axis AA is disposed at a selected angle relative to axis YY in an angular range of 0 to 45 degrees. In some embodiments, receiver 56 is connected with receiver 22 in a relatively parallel and offset orientation such that rod slots 30, 62 are disposed in a relatively parallel and offset orientation for corresponding disposal of spinal rods therein. In some embodiments, receiver 56 is connected with receiver 22 in a relatively angled and offset orientation such that rod slots 30, 62 and axes YY, AA are disposed in a corresponding orientation for disposal of spinal rods therein. In some embodiments, receiver 56 is connected to receiver 22 in a relatively angled and offset orientation such that axis AA is disposed at a selected angle relative to axis YY in an angular range of 0 to 45 degrees.

Receiver 56 includes an inner surface 66, as shown in FIG. 5. A portion of surface 66 includes a thread form 68 located adjacent arm 28 and a thread form 70 located adjacent arm 58. Thread forms 68, 70 are each configured for engagement with a coupling member, for example, a set screw (not shown), to retain spinal rod 64 within rod slot 62.

In some embodiments, receiver 56 is configured to support relative movement of a saddle (not shown). In some embodiments, the saddle includes a concave surface configured to engage at least a portion of spinal rod 64 and is moveable relative to receiver 56 in a plane, for example, a sagittal plane of a body and/or vertebrae. In some embodiments, the saddle is configured to receive and movably support spinal rod 64 such that spinal rod 64 can translate axially, rotate and/or pivot relative to receiver 56 along and about axis ZZ prior to fixation with the saddle.

In some embodiments, the saddle may be elastic and pliable in a configuration to react to forces applied and/or force changes, for example, positioning treatment, patient growth, trauma and degeneration, and/or component creep, deformation, damage and degeneration, to maintain the applied force transmitted from an implant positioned in rod slot 62 substantially constant. In some embodiments, the saddle can facilitate maintenance of a holding force on a spinal rod positioned in rod slot 62 to maintain the holding force relatively constant despite growth and changes. In some embodiments, the saddle may be disposed for movement in a multi axial configuration relative to receiver 56. In some embodiments, the saddle may be disposed in a fixed orientation relative to receiver 56.

Shaft 18 is configured to engage and/or penetrate tissue, for example, bone. Referring to FIG. 2, head 24 of shaft 18 is disposed in alignment with receiver 22 such that receiver 56 is offset from shaft 18. In some embodiments, shaft 18 includes a threaded surface to facilitate engagement with tissue. Head 24 includes a surface that includes planar surfaces, for example, flats 72 and arcuate surfaces 74 for engagement with crown 44, rings 48, 54 and/or portion 42 (as shown in FIG. 5).

In some embodiments, spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, for example, series, parallel, offset, staggered and/or alternate vertebral levels.

In some embodiments, spinal implant system 10 includes a spinal implant kit, as described herein, including the variously configured heads described herein, that are configured for selection from a plurality of alternate heads and are configured for disposal with a shaft 18 such that shaft 18 is interchangeable with the plurality of alternate heads, as described herein. In some embodiments, the spinal implant kit includes one or more components for disposal along a side of vertebrae of a patient to provide strength and facilitate surgical treatment.

In assembly, operation and use, spinal implant system 10, similar to the systems and methods described herein, can include a head 16 for connection with one or more shafts 18 and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, spinal implant system 10 comprises a spinal implant kit, which includes one or more selectable interchangeable heads, including the heads described herein, that are configured for connection with one or more selectable interchangeable shafts, including shaft 18, to facilitate disposal of bone fasteners 14 along a side of a vertebrae of a patient along a single bone fastener trajectory, as described herein. In some embodiments, the one or more selected interchangeable shafts, including shaft 18, interface with one or more selected interchangeable heads, including the heads described herein, to comprise one or more bone fasteners 14 and/or configurations. The components of bone fasteners 14 and one or a plurality of spinal implants, for example, spinal rods 32, 64 can be delivered or implanted as a pre-assembled device or can be assembled in situ. The components of spinal implant system 10 may be completely or partially revised, removed or replaced.

In some embodiments, a shaft 18 is selected from the kit of the one or more interchangeable shafts for interchangeable connection with a selected head described herein from the one or more interchangeable heads to comprise a bone fastener 14 selected for movement including a shaft 18 having uni axial and/or multi axial movement or a fixed axis relative to shaft 18.

In use, to treat a selected section of vertebrae V, as shown in FIG. 6, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Shafts 18 are fixed with tissue to engage with vertebrae V, including vertebra V1 and vertebra V2, as shown in FIG. 6. Each shafts 18 is manipulated to drive, torque, insert and/or align shafts 18 with vertebrae V along a selected trajectory. Heads 16 are disposed with shafts 18 in a snap-fit assembly. Ring 48 is disposed with upper groove 46 and ring 54 is disposed with lower groove 52 of portion 42 in a contracted orientation. Each head 16 is assembled with each shaft 18 by translating head 16, in a direction shown by arrow A in FIG. 5. Engagement of head 24 of shaft 18 with portion 42 causes a surface of head 24 to engage with ring 54 such that ring 54 is translated, in a direction shown by arrow B in FIG. 5, disposing ring 54 into expansion groove 50 in an expanded orientation. Head 24 translates further through portion 42 in the direction shown by arrow B in FIG. 5 and passes further through ring 54 as ring 54 is driven back into lower groove 52. Ring 54 resiliently contracts into its natural state around head 24.

Crown 44 is manipulated, for example, via engagement by a surgical instrument for example, a driver or inserter (not shown), to translate crown 44, in the direction shown by arrow A. An outer surface of crown 44 engages ring 48 to dispose ring 48 into expansion groove 50 such that ring 48 resiliently opens into its natural orientation. Ring 48 is oriented for abutting and/or contacting engagement with ring 54 to resist and/or prevent translation of ring 54 from lower groove 52 into expansion groove 50, and thus providing fixed connection of the components of bone fastener 14 including permanent capture of head 24 of shaft 18.

A spinal rod, for example, a spinal rod 32 is delivered to the surgical site adjacent vertebrae V. Spinal rod 32 is disposed with each receiver 22 of each head 16, as shown in FIG. 6. Set screws (not shown) engage with a surgical instrument, for example, a driver (not shown), which advances the set screws into engagement with each receiver 22 to lock spinal rod 32 with each receiver 22 to attach spinal rod 32 with vertebrae V.

A spinal rod, for example, a spinal rod 64 is delivered to the surgical site adjacent vertebrae V. Spinal rod 64 is disposed with each receiver 56 of each head 16, as shown in FIG. 6. Set screws (not shown) engage with a surgical instrument, for example, a driver (not shown), which advances the set screws into engagement with each receiver 56 to lock spinal rod 64 with each receiver 56 to attach spinal rod 64 with vertebrae V.

In some embodiments, the spinal constructs of spinal implant system 10, as described herein, are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

Figure 9:
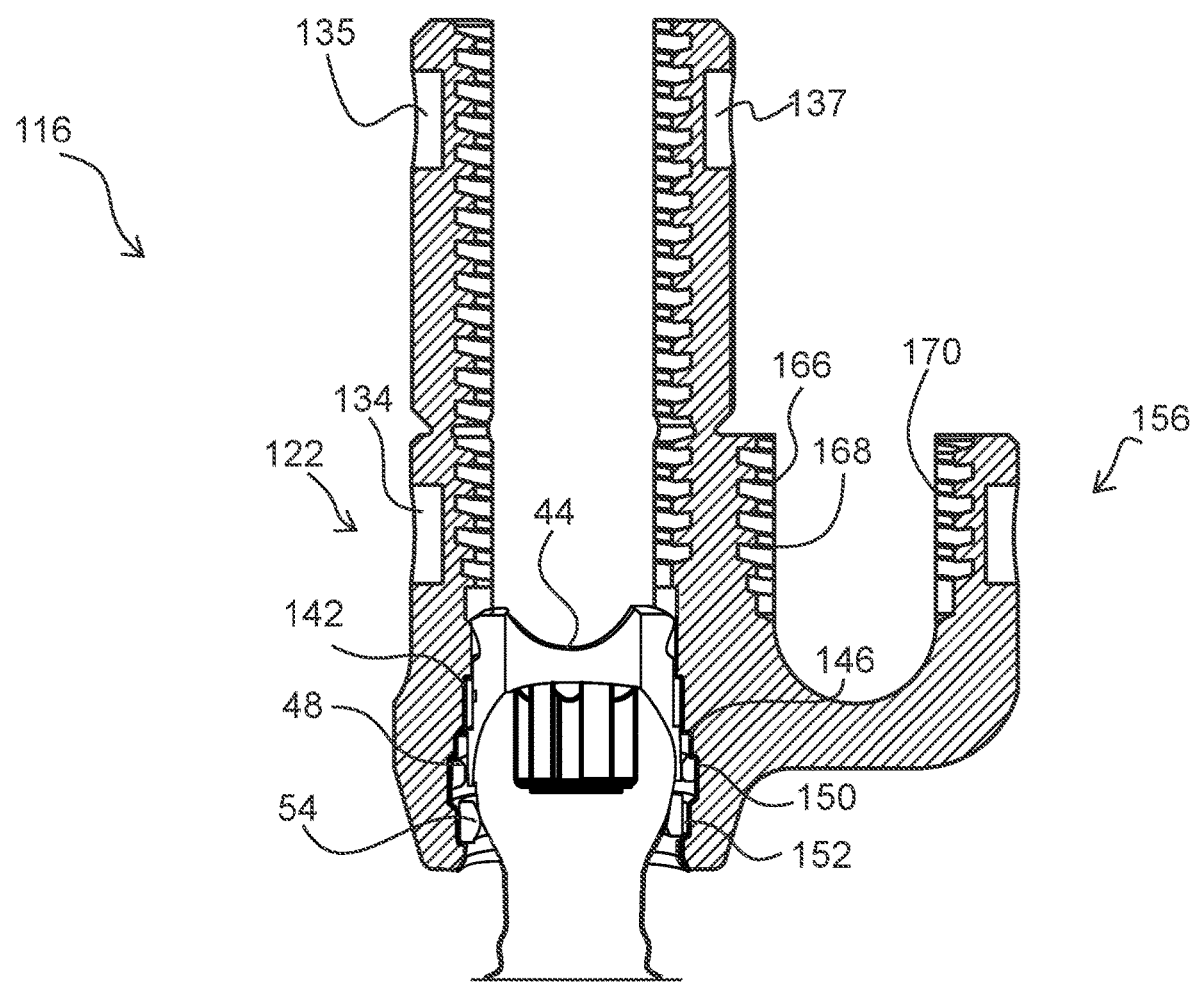
FIG. 9 is a cross section view of the components of the system shown in FIG. 7.

In some embodiments, bone fastener 14 includes a head 116, as shown in FIGS. 7-9, similar to head 16 described herein. Head 116 is configured for engagement with shaft 18. In some embodiments, head 116 is selected from a plurality of alternate heads and is configured for disposal with shaft 18 such that shaft 18 is interchangeable with the plurality of alternate heads 16, 116.

Head 16 includes a body 120, as shown in FIG. 7. Body 120 includes a surface that defines a receiver 122. Receiver 122 is disposed in axial alignment with head 24 of shaft 18. Receiver 122 defines an axis BB and includes an arm 126 and an arm 128 spaced apart from arm 126. In some embodiments, shaft 18 is selectively movable relative to receiver 122 and/or axis BB through an angular range and disposable at a selected angle relative to receiver 122 and/or axis BB, similar to that described herein.

Arms 126, 128 define an implant cavity, for example, a rod slot 130 therebetween. Rod slot 130 is configured for top loading of a spinal implant, for example, spinal rod 32. In some embodiments, rod slot 130 is configured for side loading or has a closed configuration. Arms 126, 128 each extend parallel to axis BB, as shown in FIG. 7. Arms 126, 128 each include an arcuate outer surface extending between a pair of side surfaces. In some embodiments, at least one of the outer surfaces and/or the side surfaces of arms 126, 128 have at least one recess or cavity 134 therein configured to receive an insertion tool, compression instrument and/or surgical instruments for manipulating bone fastener 14, as shown in FIG. 7.

Rod slot 130 is substantially U-shaped. Rod slot 130 defines and extends along an axis CC oriented transverse to axis BB, as shown in FIG. 7. Receiver 122 includes an inner surface 136, as shown in FIG. 8. A portion of surface 136 includes a thread form 138 located adjacent arm 126 and a thread form 140 located adjacent arm 128. Thread forms 138, 140 are each configured for engagement with a coupling member, for example, a set screw (not shown), to retain a spinal rod within rod slot 130.

Arm 126 includes a break away tab 127 that is frangibly connected to arm 126 at a break off portion 129, as shown in FIG. 8. Portion 129 is fabricated from a fracturing and/or frangible material such that manipulation of tab 127 relative to arm 126 can fracture and separate tab 127 from arm 126 along portion 129 at a predetermined force and/or torque limit, as described herein. Arm 128 includes a break away tab 131 that is frangibly connected to arm 128 at a break off portion 133. Portion 133 is fabricated from a fracturing and/or frangible material such that manipulation of tab 131 relative to arm 128 can fracture and separate tab 131 from arm 128 along portion 133 at a predetermined force and/or torque limit, as described herein. In some embodiments, an outer surface of tabs 127, 131 define at least one recess or cavity 135, 137 therein configured to receive an insertion tool, compression instrument and/or surgical instruments for manipulating bone fastener 14, as shown in FIG. 9.

In some embodiments, tab 127, 131 are configured to facilitate reduction of one or more spinal rods, as described herein, with a bone fastener and/or vertebrae. Tabs 127, 131 are configured to extend an overall height of bone fastener 14 and facilitate disposal of one or more spinal rods with receiver 122. In some embodiments, tabs 127, 131 can fracture and separate at a predetermined force or torque limit, which may be in a range of approximately 2 Newton meters (N-m) to 8 Nm. In some embodiments, tabs 127, 131 and/or arms 126, 128 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 127, 131 from arms 126, 128.

Receiver 122 includes a distal portion 142 configured for disposal of crown 44, as shown in FIG. 9. In some embodiments, a set screw (not shown) is configured for engagement with spinal rod 32 to facilitate fixation and/or locking of spinal rod 32 with receiver 122, as described herein.

An inner surface of portion 142 defines a circumferential upper groove 146, as shown in FIG. 9, for disposal of a resilient member, for example, ring 48. Ring 48 is contractable in upper groove 146. The inner surface of portion 142 defines an expansion groove 150. The inner surface of portion 142 defines a circumferential lower groove 152 for disposal of a resilient member, for example, ring 54. Ring 54 is expandable in expansion groove 150.

Head 116 includes a receiver 156, as shown in FIG. 7, similar to receiver 122, described herein. Receiver 156 defines an axis DD, as shown in FIG. 7 and includes arm 128 and an arm 158, as shown in FIG. 7. Arm 158 includes an arcuate outer surface extending between a pair of side surfaces. In some embodiments, at least one of the outer surfaces and/or the side surfaces of arm 158 have at least one recess or cavity 160 therein configured to receive an insertion tool, compression instrument and/or surgical instruments for manipulating bone fastener 14, as shown in FIG. 8. In some embodiments, shaft 18 is selectively movable relative to receiver 156 and/or axis DD through an angular range and disposable at a selected angle relative to receiver 156 and/or axis DD, similar to that described herein.

Arms 128, 158 are spaced apart to define an implant cavity, for example, a rod slot 162 therebetween. Receiver 122 is connected to receiver 156 via head 116 and arm 128 in a side by side and/or relatively parallel and adjacent orientation. As such, rod slots 130, 162 are disposed in a side by side and/or relatively parallel and adjacent orientation, and axis DD, and an axis EE are disposed in a relatively parallel orientation, for corresponding disposal of spinal rods therein, as shown in FIG. 7. Rod slot 162 is configured for top loading of spinal rod 64. Rod slot 162 is disposed separate and apart from rod slot 130, and is substantially U-shaped. Rod slot 162 defines and extends along axis EE oriented parallel to axis CC.

Receiver 156 includes an inner surface 166, as shown in FIG. 9. A portion of surface 166 includes a thread form 168 located adjacent arm 128 and a thread form 170 located adjacent arm 158. Thread forms 168, 170 are each configured for engagement with a coupling member, for example, a set screw (not shown), to retain spinal rod 64 within rod slot 162. In some embodiments, receiver 156 is configured to support relative movement of a saddle (not shown).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a head including a first receiver defining a longitudinal axis, an implant cavity and a distal portion defining a plurality of adjacent grooves, the head further including a second receiver defining an implant cavity, a bottom surface of the second receiver being axially offset relative to a bottom surface of the first receiver;
   a first resilient member configured for disposal within the plurality of adjacent grooves;

a second resilient member configured for disposal within the plurality of adjacent grooves; and a shaft being aligned with the first receiver and configured to engage tissue.

2. The bone fastener as recited in claim 1, wherein the implant cavities each include a rod slot such that the rod slot of the first receiver is disposed in a parallel and adjacent orientation relative the rod slot of the second receiver.

3. The bone fastener as recited in claim 1, wherein the plurality of adjacent grooves includes a first groove, a second groove and a third groove, and the first resilient member including a first ring and the second resilient member including a second ring.

4. The bone fastener as recited in claim 3, wherein the first ring is configured to contract within the first groove and to expand within the second groove.

5. The bone fastener as recited in claim 3, wherein the second ring is configured to expand within the second groove and contract within the third groove.

6. The bone fastener as recited in claim 3, wherein the head is manually engageable with the second ring to connect the head with the shaft in a non-instrumented snap-fit assembly.

7. The bone fastener as recited in claim 1, wherein the first resilient member includes a first ring and the second resilient member includes a second ring, the first ring and the second ring each defining a gap.

8. The bone fastener as recited in claim 1, wherein the first receiver is integrally formed with the second receiver.

9. The bone fastener as recited in claim 1, wherein the head includes a first arm and a second arm that define the first implant cavity, and a third arm and the second arm define the second implant cavity.

10. The bone fastener as recited in claim 9, wherein the arms comprise extended reduction tabs.

11. The bone fastener as recited in claim 10, wherein the tabs include break off portions.

12. The bone fastener as recited in claim 1, wherein the bone fastener includes a part including a crown engageable with the first receiver, the first resilient member and a head of the shaft.

13. A bone fastener comprising:

a head including arms that define a first rod receiver defining a longitudinal axis and a slot, and a second rod receiver defining a slot, the slots being separate and adjacent, the head further including a distal portion defining a plurality of adjacent grooves, a bottom surface of the second rod receiver being axially offset relative to a bottom surface of the first rod receiver;

a shaft attached with the head for multi-axial movement, the shaft being aligned with the first rod receiver and configured to engage tissue;

a first ring configured for disposal within the plurality of adjacent grooves;

a second ring configured for disposal within the plurality of adjacent grooves; and a crown disposed with the first rod receiver slot.

14. The bone fastener as recited in claim 13, wherein the plurality of adjacent grooves includes a first groove, a second groove and a third groove.

15. The bone fastener as recited in claim 14, wherein the first ring is configured to contract within the first groove and to expand within the second groove.

16. The bone fastener as recited in claim 14, wherein the second ring is configured to expand within the second groove and contract within the third groove.

17. The bone fastener as recited in claim 13, wherein the head is manually engageable with the second ring to connect the head with the shaft in a non-instrumented snap-fit assembly.

18. A spinal implant system comprising:

a bone fastener having a head including a first rod receiver defining a longitudinal axis and a slot, and a distal portion defining a plurality of adjacent grooves, the head further including a second rod receiver defining a slot, a bottom surface of the second rod receiver being axially offset relative to a bottom surface of the first rod receiver, a first resilient member and a second resilient member being disposable within the plurality of adjacent grooves, and a shaft being aligned with the first rod receiver and configured to engage tissue;

a first spinal rod; and a second spinal rod.

19. The spinal implant system as recited in claim 18, wherein the first resilient member includes a first ring and the second resilient member includes a second ring, the first ring and the second ring each defining a gap.

20. The spinal implant system as recited in claim 18, wherein the head includes arms having extended reduction tabs with break off portions.

* * * * *